United States Patent [19]

Kitaguchi et al.

[11] Patent Number: 5,252,706

[45] Date of Patent: Oct. 12, 1993

[54] PEPTIDE DERIVATIVE AMPHIPHATIC COMPOUND, INTERMEDIATE THEREOF AND LIPOSOME AND FILM COMPRISING PEPTIDE DERIVATIVE AMPHIPHATIC COMPOUND

[75] Inventors: Hiroshi Kitaguchi; Ryoichi Nemori, both of Kanagawa, Japan

[73] Assignee: Fuji Photo Film Co., Ltd., Kanagawa, Japan

[21] Appl. No.: 681,301

[22] Filed: Apr. 8, 1991

[30] Foreign Application Priority Data

Apr. 9, 1990 [JP] Japan .................................. 2-93482
Jul. 31, 1990 [JP] Japan .................................. 2-203218

[51] Int. Cl.$^5$ ..................... C07K 7/06; C07C 233/00; C07C 237/12
[52] U.S. Cl. .................................. 530/329; 530/331; 530/330; 564/152; 564/159; 564/192; 564/199; 564/201; 564/504; 554/106; 554/112; 554/35; 554/51; 554/56; 554/57
[58] Field of Search .................. 428/402.2, 338; 424/450; 260/403, 404, 407; 530/345, 359, 402, 300, 329, 330, 331; 554/106, 109, 112, 103; 564/152, 159, 192, 503, 504, 199, 201

[56] References Cited

U.S. PATENT DOCUMENTS

| | | | |
|---|---|---|---|
| 2,236,516 | 4/1941 | Cahn et al. | 554/111 |
| 3,239,546 | 3/1966 | Rogier | 564/159 |
| 4,166,132 | 8/1979 | Kraska | 564/504 |
| 4,863,941 | 9/1989 | Barner | 554/106 |

FOREIGN PATENT DOCUMENTS

2347336 11/1977 France .

OTHER PUBLICATIONS

European Search Report.
Chemical Abstracts, vol. 92, 1980, p. 547, abstract No. 93919u, Columbus, Ohio, US; & DE-A-2 820 892 (Nattermann, A., Und Cie. GmbH) Nov. 22, 1979.
Scientific American, vol. 256, No. 1, Jan. 1987, pp. 91-99, New York, US; M. J. Ostro: "Liposomes".
J. Am. Chem Soc., vol. 108, 1986, pp. 487-490; R. Neumann et al: "Peptide Liposomes from amphiphilic amino acids".
Patent Abstracts of Japan, vol. 12, No. 202 (C-503) [3049], Jun. 10, 1988; JP-A-63 2921 (Yamanouchi Pharmaceut. Co., Ltd.) Jan. 7, 1988, corresponding to JP-A-61-144062.

*Primary Examiner*—Robert L. Stoll
*Assistant Examiner*—John M. Covert
*Attorney, Agent, or Firm*—Sughrue, Mion, Zinn, Macpeak & Seas

[57] ABSTRACT

A peptide derivative amphiphatic compound or N-terminal salt thereof represented by formula (I):

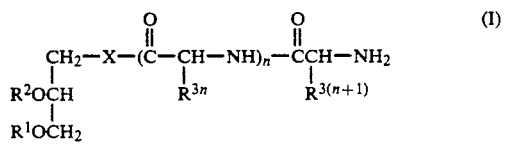

wherein $R^1$ and $R^2$ each represents a straight-chain or branched alkyl or acyl group having 8 to 24 carbon atoms optionally having a substituent or an unsaturated group; X represents —O— or —NH—; $R^{3n}$ and $R^{3(n+1)}$ each represents an α—amino acid side chain; n is an integer of from 0 to 5; the compound may be a racemic compound or an optically active compound when the compound has an asymmetric carbon atom; and the N-terminal salt of the compound optionally forms with an acid component; an intermediate thereof, a liposome comprising said peptide derivative amphiphatic compound and a film consisting of a monolayer or multilayers comprising the peptide derivative amphiphatic compound are disclosed.

1 Claim, 5 Drawing Sheets

PEPTIDE DERIVATIVE AMPHIPHATIC COMPOUND, INTERMEDIATE THEREOF AND LIPOSOME AND FILM COMPRISING PEPTIDE DERIVATIVE AMPHIPHATIC COMPOUND

FIELD OF THE INVENTION

This invention relates to an oligopeptide derivative having amphiphatic properties when bound to a hydrophobic group, a liposome and a monolayer each comprising said oligopeptide derivative as a film component.

BACKGROUND OF THE INVENTION

A liposome is a closed vesicle comprising a lipid bimolecular film. It is considered that a natural biomembrane has a lipid bimolecular structure and thus liposomes have been widely used as a biomembrane model in studies on physicochemical properties of biomembranes. Furthermore, a number of substances can be enclosed in the internal aqueous layer or within the membrane of a liposome and then fused with a cell or incorporated into a cell. Thus liposomes have been used as a carrier for transporting substances to and into cells.

Attempts have been widely made to apply liposomes to various purposes in the fields of, for example, biology, medicine and pharmacology, so as to employ liposomes as a carrier for transporting enzymes or cancerocidal substances, to use liposomes for immunological purposes, to utilize the interaction of liposomes with cells or to apply liposomes as a drug delivery system.

Although liposomes are widely applicable to various purposes as described above, it has been recognized that liposomes have a brittle membrane structure, such that a chemical or physical change, in the lipids, constituting the membrane, causes some irreglularities in the orientation of the membrane. This brings about the leakage of the content of the liposomes, or the association or aggregation of liposomes with each other. As a result, a precipitate is formed.

In order to overcome this problem, a number of attempts to form a vesicle using synthetic amphiphatic compounds as analogs of naturally occurring phospholipids have been reported (refer to, for example, "Liposome," ed. by Nojima, Sunamoto and Inoue, Nankodo, Chap. 8). However none of the vesicles thus obtained is satisfactory as a drug carrier from the viewpoint of stability and lack of toxicity to the human body.

Known examples of an amphiphatic compound having an oligopeptide in the hydrophilic moiety and two long-chain alkyl groups in the hydrophobic moiety include those reported by Ihara et al. [Polym. Commun., 27, 282 (1986); Polymer J., 18, 463 (1986); Chem. Lett., (1984), 1713; and J. Jap. Chem., (1987), 543] and reported by Shimizu et al. (Chem. Lett., (1989), 1341; Thin Solid Films, 180 (1989), 179; JP-A-2-69498 and JP-A-2-71836] (the term "JP-A" as used herein means an "unexamined published Japanese patent application"). However none of these amphiphatic compounds is suitable as a drug carrier, since either it fails to form a vesicle or a monolayer or monolayer vesicle, if formed, is easily converted into other structures.

On the other hand, it is expected that molecular assemblies comprising a monolayer having a molecular orientation or multilayers, which are ultra-thin and dense, are widely applicable to materials for electronics devices and materials for protecting surfaces as well as to functional films for sensors based on the selective permeability of a gas molecule or an ion and permeation-controlling films for delivering materials.

The Langmuir-Blodgett ("LB") technique has been commonly known as a method for laminating a monolayer comprising amphiphatic compound molecules formed on a gas/liquid interface on a substrate. Recently, various LB films produced by this technique have been widely employed as organic ultra-thin films [refer to Kotai Butsuri, 17 (12), 45 (1982)].

Although molecular assemblies including LB films exert various functions based on the orientation of molecules and the ultra-thin properties, they have a highly delicate film structure from a physical standpoint and thus are liable to degradation or decomposition. It is observed in the cases of some of such compounds, furthermore, that the film structures suffer from many defects or irregularities and thus high density cannot be achieved. Therefore it is required for all uses to physically strengthen the film structures of these molecular assemblies to thereby provide uniform and highly dense films.

An effective means for physically strengthening the film structure of a molecular assembly is crosslinkage or polymerization of molecules.

Relating to the polymerization of, for example, LB films, conventional polymerizable compounds and polymerization modes are summarized by H. Bader et al. [Advances in Polymer Science, 64, 1 (1985)] and R. Buschl et al. [Macromol. Chem. Suppl., 6, 245 (1984)].

Polymerizable amphiphatic compounds have been frequently investigated. At the early stage of these studies, the major means employed comprised polymerizing unsaturated vinyl diene and diacetylene compounds, which were selected as polymerizable compounds, by irradiation using UV or rays such as γ-rays. Although the polymers obtained by these methods had fast structures, the order of the molecular arrangement was poorly maintained after cleavage of unsaturated bonds.

As A. Laschewsky and H. Ringsdorf [Macromolecules, 21, 1936 (1988)] point out, the number of well-ordered polymerizable compounds is very limited, because the orientation of a film is significantly affected by the length of an alkyl chain and the terminal hydrophilic group.

A. Laschewsky et al. further disclose [J. Am. Chem. Soc., 109, 788 (1987)] that polymerizable groups in various amphiphatic compounds having unsaturated bonds, which are useful in, for example, radiation polymerization, should be kept via spacer groups in order to maintain the order of molecular arrangement. Furthermore, JP-A-57-159506 shows an example of the application of a monolayer and multilayer polymeric film of an unsaturated compound (surfactant) produced via radiation polymerization as an ultrafiltration membrane.

Known techniques for polymerizing these compounds having unsaturated bonds via radiation suffer from the following problems. Namely, one problem resides in the fact that a specific molecular design strategy (for example, inserting a spacer group) is required in order to avoid some irregularities in the molecular orientation or irregular aggregation and precipitation of molecules caused by the polymerization. A second problem resides in the fact that the irradiation with UV or γ-ray would frequently induce the decomposition or denaturation of various additives which are present together with the polymerizable amphiphatic compounds. A third problem resides in the fact that the film thus obtained via such a polymerization usually has extremely poor biocompatibility, which restricts the types and number of applications of such a product in living tissues to, for example, a permeation-controlling membrane for drugs.

Therefore, J. Am. Chem. Soc., 109, 4419 (1987) proposes a method for forming disulfide bond via the oxidative polymerization of dithiol without using radiation. Alternately, it is effective to radical-polymerize the above-mentioned compounds having unsaturated bonds in the presence of an initiator. In these methods, however, an initiator used at the polymerization needs to be removed from the film system after completion of the polymerization. In addition, the effects of the uses of an initiator involving redox agents on coexisting substances should be taken into consideration which initiator may have optimental effects on other components of such films.

Furthermore, the condensation polymerization of a molecular film of an amino acid derivative has been attempted in the presence of carbodiimide in order to improve the polymerization mode and enhance the biocompatibility [refer to J. A., Chem. Soc., 108, 487 (1986).] However this method cannot be easily performed too, since there is a problem of the residual condensing agent and by-products and it is required to control the efficiency of the condensation reaction.

SUMMARY OF THE INVENTION

It is an object of the present invention to provide an oligopeptide derivative, to which amphiphatic properties are imparted by binding to a hydrophobic group capable of forming a stable monolayer liposome, having the properties of showing negligible leakage of a drug contained therein and scarcely suffering from association, aggregation and precipitation, as well as an intermediate thereof.

It is another object of the present invention to provide a liposome which comprises the oligopeptide derivative as a film component and which shows little leakage of a drug contained therein.

It is another object of the present invention to provide a highly dense and substantially faultless film by taking advantage of the two-dimensional orientation formed by intermolecular hydrogen bonds of an oligopeptide incorporated in lipid molecules, different from the polymerization effected in the above-mentioned conventional methods.

Furthermore, it is another object of the present invention to provide a film which has excellent biocompatibility and is suitable for carrying biosubstances such as proteins.

These objects of the present invention have been achieved by a compound or N-terminal salt thereof represented by the general formula (I), a liposome comprising said compound as a film component or a monolayer or multilayers comprising the compound of the general formula (I).

In the above general formula (I), $R^1$ and $R^2$ represent each a straight-chain, branched alkyl or acyl group having 8 to 24, and preferably 12, 14, 16 or 20, carbon atoms, optionally having a substituent or an unsaturated group. Substituent groups can be, e.g., alkylcarbonyl groups, alkoxycarbonyl groups, halogen atoms and aryl groups. Unsaturated groups can contain double and triple bonds wherein two or more unsaturated bonds may be present in each of $R^1$ and $R^2$. Examples of $R^1$ and $R^2$, which can be the same or different, include dodecyl, tetradecyl, hexadecyl, myristoyl and palmitoyl groups.

X can represent —O— or —NH —.

$R^{3n}$ and $R^{3(n+1)}$ can each represent a side chain of an α-amino including a side chain of one of the of 20 α-amino acids occurring in nature (refer to, for example, Creighton, "PROTEINS," Freeman Co. (1984)) and analogues and derivatives thereof. Preferable examples thereof among amino acid side chains according to the present invention include a hydrogen atom, and side chain residues of amino acids which are more hydrophilic than glycine, for example, In $R^{3(n+1)}$, $(n+1)$ is a number of one figure. When $n=5$, for example, $R^{3(n+1)}$ corresponds to $R^{36}$. $R^{31}$, $R^{32}$, , $R^{3(n+1)}$ may be either the same or different from each other.

n is an integer of from 0 to 5, preferably 0, 1, 2 and 3.

An asymmetric carbon atom can be present in the compound and the compound can be either a racemic compound or an optically active one. It is frequently advantageous, from the viewpoint of stability or handling, that the amino group at the terminal of the molecule forms a salt together with an appropriate acid component. Preferable examples of the acid component include trifluoroacetic acid, hydrogen chloride and hydrogen bromide.

DETAILED DESCRIPTION OF THE INVENTION

Examples of the compound represented by the general formula (I) are given below, although the present invention is not be construed as limited thereby.

| Compound | R¹ | R² | R³¹ | R³² | R³³ | R³⁴ | HB | X |
|---|---|---|---|---|---|---|---|---|

Structure for compounds (1)-(3):

$$R^1-O-CH_2-C(OR^2)(H)-CH_2-X-C(=O)-C(R^{31})(H)-NH_2 \cdot H^{\oplus}B^{\ominus}$$

(wherein B⁻ represents the conjugated base of an acid HB.)

| Compound | R¹ | R² | R³¹ | HB | X |
|---|---|---|---|---|---|
| (1) | C₁₄H₂₉ | C₁₄H₂₉ | H | HCl | —O— |
| (2) | " | " | —CH₂OH | | HCl | —O— |
| (3) | " | " | —CH₂CO₂H | HCl | —NH— |

Structure for compounds (4)-(15):

$$R^1-O-CH_2-C(OR^2)(H)-CH_2-X-C(=O)-CH_2-NH-C(=O)-C(R^{32})(H)-NH_2 \cdot H^{\oplus}B^{\ominus}$$

| Compound | R¹ | R² | R³² | HB | X |
|---|---|---|---|---|---|
| (4) | C₁₄H₂₉ | C₁₄H₂₉ | H | HCl | —NH— |
| (5) | C₁₄H₂₉ | C₁₄H₂₉ | H | CF₃CO₂H | —NH— |
| (6) | C₁₄H₂₉ | C₁₄H₂₉ | H | HCl | —O— |
| (7) | C₁₄H₂₉ | C₁₄H₂₉ | —CH₂C(=O)NH₂ | CF₃CO₂H | —O— |
| (8) | C₁₄H₂₉ | C₁₄H₂₉ | H | CF₃CO₂H | —O— |
| (9) | C₁₆H₃₃ | C₁₆H₃₃ | H | CF₃CO₂H | —O— |
| (10) | C₁₆H₃₃ | C₁₆H₃₃ | H | HCl | —O— |
| (11) | C₁₅H₃₁C(=O)— | C₁₅H₃₁C(=O)— | H | CF₃CO₂H | —O— |
| (12) | C₁₃H₂₇C(=O)— | C₁₃H₂₇C(=O)— | H | HCl | —O— |
| (13) | C₁₄H₂₉ | C₁₄H₂₉ | —CH₂OH | HCl | —O— |
| (14) | C₁₅H₃₁C(=O)— | C₁₅H₃₁C(=O)— | H | HCl | —O— |
| (15) | C₁₂H₂₅C(=O)— | C₁₂H₂₅C(=O)— | H | CF₃CO₂H | —O— |

Structure for compounds (16)-(27):

$$R^1-O-CH_2-C(OR^2)(H)-CH_2-X-C(=O)-CH_2-NH-C(=O)-C(R^{32})(H)-NH-C(=O)-C(R^{33})(H)-NH_2 \cdot H^{\oplus}B^{\ominus}$$

| Compound | R¹ | R² | R³² | R³³ | HB | X |
|---|---|---|---|---|---|---|
| (16) | C₁₄H₂₉ | C₁₄H₂₉ | H | H | CF₃CO₂H | —O— |
| (17) | " | " | H | —CH₂OH | " | —O— |
| (18) | C₁₆H₃₃ | C₁₆H₃₃ | H | H | HCl | —O— |
| (19) | C₁₄H₂₉ | C₁₄H₂₉ | —CH₂OH | —CH₂OH | HCl | —O— |
| (20) | C₁₃H₂₇C(=O)— | C₁₃H₂₇C(=O)— | H | H | CF₃CO₂H | —O— |
| (21) | C₁₄H₂₉ | C₁₄H₂₉ | H | —CH₂CO₂H | — | —O— |
| (22) | " | " | H | H | HCl | —O— |
| (23) | " | " | H | —CH₂C(=O)NH₂ | CF₃CO₂H | —O— |
| (24) | C₁₃H₂₇C(=O)— | C₁₃H₂₇C(=O)— | H | —CH₂OH | HCl | —O— |
| (25) | C₁₅H₃₁C(=O)— | C₁₅H₃₁C(=O)— | H | —CH(OH)CH₃ | CF₃CO₂H | —O— |
| (26) | C₁₄H₂₉ | C₁₄H₂₉ | H | —CH₂CH₂CH₂CH₂NH₂ | CF₃CO₂H | —NH— |
| (27) | C₁₂H₂₅ | C₁₂H₂₅ | H | —CH₂CH₂CO₂H | — | —O— |

Structure for subsequent compounds:

$$R^1-O-CH_2-C(OR^2)(H)-CH_2-X-C(=O)-CH_2-NH-C(=O)-C(R^{32})(H)-NH-C(=O)-C(R^{33})(H)-NH-C(=O)-C(R^{34})(H)-NH_2 \cdot H^{\oplus}B^{\ominus}$$

| Compound | $R^1$ | $R^2$ | $R^{31}$ | $R^{32}$ | $R^{33}$ | $R^{34}$ | HB | X |
|---|---|---|---|---|---|---|---|---|
| (28) | $C_{14}H_{29}$ | $C_{14}H_{29}$ |  | H |  | H | H | $CF_3CO_2H$ | —O— |
| (29) | " | " |  | " |  | " | —$CH_2OH$ | HCl | —O— |
| (30) | " | " |  | " |  | " | H | HCl | —NH— |

| Compound | $R^1$ | $R^2$ | $R^{31}$ | $R^{32}$ | $R^{33}$ | $R^{34}$ | HB | X |
|---|---|---|---|---|---|---|---|---|
| (31) | $C_{14}H_{29}$ | $C_{14}H_{29}$ | —$CH_2OH$ | —$CH_2OH$ |  |  | HCl | —O— |
| (32) | $C_{16}H_{33}$ | $C_{16}H_{33}$ | —$CH_2OH$ | —$CH_2OH$ |  |  | HCl | —O— |
| (33) | $C_{13}H_{27}\overset{O}{\underset{\|}{C}}-$ | $C_{13}H_{27}\overset{O}{\underset{\|}{C}}-$ | —$CH_2OH$ | $CH_2OH$ |  |  | HCl | —O— |

The amphiphatic compound of the present invention may be prepared using known methods, e.g., by synthesizing an oligopeptide moiety whose N-terminal and side chain are blocked, and then condensing the obtained product with glycerol substituted at the 1- and 2-positions [general formula (III)] or an amino derivative thereof [a compound of general formula (II) wherein Y is a hydrogen atom]. Alternately, compounds represented by the general formula (II) or (III) may be successively condensed with amino acids whose N-terminii and side chains are blocked [the former method is called a fragment condensation method, while the latter one is called a stepwise elongation method, refer to Izumiya et al. "Peptide Gosei no Kiso to Jikken," Maruzen, Chap. 8 (1985).]

$$\begin{array}{l} CH_2-NH-Y \\ | \\ CH-OR^2 \\ | \\ CH_2-OR^1 \end{array} \quad (II)$$

$$\begin{array}{l} CH_2-OH \\ | \\ CH-OR^2 \\ | \\ CH_2-OR^1 \end{array} \quad (III)$$

wherein $R^1$ and $R^2$ are the same as those defined in general formula (I); and each compound can be either a racemic compound or an optically active one regarding the asymmetric carbon atom in the molecule.

Compounds of the general formula (II) are useful as an intermediate of the compound of the general formula (I).

Compounds represented by the general formula (III) may be synthesized known methods, for example, by a method described in J. Am. Chem. Soc., 63, 3244 (1941). Alternately, a commercially available compound may be employed.

Compounds of general formula (II), wherein Y is a hydrogen atom, can be synthesized using known methods, e.g., by converting the hydroxyl group of the compound of the general formula (III) into an amino group, for example, by methods described in "Shin Jikken Kagaku Koza", ed. by J. Soc. of Chem., 14 (III), 1332–1399 (Maruzen) (1978). Typical examples of such known methods include (1) converting the hydroxyl group into a p-toluenesulfonate followed by substituting with phthalimide potassium or treating with hydrazine (Gabriel's method); and (2) substituting the p-toluenesulfonate with an azide followed by hydrogenating.

Compounds represented by the general formula (II), wherein Y is a hydrogen atom, can be purified and preserved in the form of salts together with an appropriate acid component, since such compounds are generally in a waxy state and thus are difficult to purify and, furthermore, easily undergo transacylation when $R^1$ and $R^2$ are acyl groups. Preferable examples of acid components include trifluoroacetic acid, acetic acid, hydrogen chloride and hydrogen bromide. When the amino group is protected, the aforesaid problems would be scarcely observed. Preferable examples of the protecting groups include t-butyloxycarbonyl (tBoc) group and benzyloxycarbonyl (CBZ) group.

Now Examples of compounds according to the present invention will be given. Amino acids and abbreviations thereof are in accordance with those commonly employed in the art [refer to, for example, "Peptide Gosei no Kiso to Jikken," ed. by Izumiya et al., (Maruzen), as cited above.] "A liquid crystal phase transition point" as used hereinafter means the temperature at which a crystal phase melts to become a liquid phase, which was measured by using DSC 100 (produced by Seiko Instruments Inc.).

SYNTHETIC EXAMPLE 1: SYNTHESIS OF COMPOUND (8)

Commercially available GlyGly was converted into amino group protected tBoc-GlyGly in accordance with known methods, e.g., as described in "Peptide Gosei no Kiso to Jikken," ed. by Izumiya et al., (Maruzen).

1.39 g (6 mmol) of tBoc-GlyGly, 2.42 g (5 mmol) of 1,2-o-ditetradecyl-syn-glycerol and 60 mg of N,N-dimethylaminopyridine were dissolved in 20 ml of DMF (N, N-dimethylformamide) and 10 ml of methylene chloride. To the solution thus formed, was added 1.3 g of DCC (dicyclohexylcarbodiimide) under cooling with water and stirring. Then the mixture was stirred at room temperature for 24 hours. The dicyclohexyl urea thus precipitated was filtered and methylene chloride was distilled off from the filtrate under reduced pressure. 50 ml of ethyl acetate was added to the residue followed by successively washed with a 10% aqueous solution of citric acid, with water and saline and separating. The dicyclohexyl urea precipitated again in the ethyl acetate phase and was filtered to produce a filtrate which was then concentrated. Then the residue from the concentrated filtrate was purified by silica gel chromatography (n-hexane/ethyl acetate=2/1) to thereby give 3.37 g (4.8 mmol) of the compound (8) in a tBoc-protected form having a yield of 90%.

3.37 g of this protected product as compound (8) was dissolved in 60 ml of methylene chloride. After adding 30 ml of trifluoroacetic acid, the mixture was stirred at room temperature for 30 minutes. Then the solvent methylene chloride was distilled off under reduced pressure and the residue was recrystallized from a solvent mixture (ethyl acetate/acetonitrile =1/1) to thereby give 2.87 g (4.03 mmol) of the compound (8) having a yield of 84% and a liquid crystal phase transition point of 79° C.

SYNTHETIC EXAMPLE 2: SYNTHESIS OF COMPOUND (16)

tBoc-GlyGly synthesized n the above Synthetic Example 1 was condensed with commercially available Gly-oBzl p-toluenesulfonate by DCC. Further, the obtained condensate was hydrogenated with 10% palladium carbon to thereby give tBoc-GlyGlyGly.

Starting from 2.2 g (8 mmol) of the tBoc-GlyGlyGly and 3.88 g (8 mmol) of 1,2-o-ditetradecyl-syn-glycerol, the procedure of Synthetic Example 1 was repeated. After purifying by silica gel column chromatography (ethyl acetate/chloroform =3/2), 4.35 g (5.75 mmol) of the compound (16) was obtained in a tBoc-protected form, having a yield of 72%.

Then the protecting group was removed by treating with trifluoroacetic acid, similar to Synthetic Example 1. After recrystallizing from ethyl acetate, 4.3 g (5.58 mmol) of the compound (16) was obtained having a yield of 97% and a liquid crystal phase transition point of 97° C.

SYNTHETIC EXAMPLE 3: SYNTHESIS OF COMPOUND (20)

Starting from 1.37 g (5 mmol) of tBoc-GlyGlyGly as prepared in Synthetic Example 2 above, and 2.56 g (5 mmol) of 1,2-o-dimyristoyl-syn-glycerol, the procedure of Synthetic Example 1 was repeated. After purifying by silica gel column chromatography (ethyl acetate/chloroform =25/10), 2.9 g (3.7 mmol) of the compound (20) was obtained in a tBoc-protected form having a yield of 74%.

Then the protecting group was removed from 2.8 g (3.87 mmol) of the protected product by treating with trifluoroacetic acid, according to Synthetic Example 1. After recrystallizing from ethyl acetate, 2.58 g (3.23 mmol) of the compound (20) was obtained, having a yield of 91% and a liquid crystal phase transition point of 88° C.

SYNTHETIC EXAMPLE 4: SYNTHESIS OF COMPOUND (9)

The same condensation and deprotection procedures as those described in Synthetic Example 1 were performed except that the 1,2-o-ditetradecyl-syn-glycerol was replaced with 1,2-o-dihexadecyl-syn-glycerol to obtain compound (9) having a liquid crystal phase transition point of 82° C.

SYNTHETIC EXAMPLE 5: SYNTHESIS OF COMPOUND (17)

1.06 g (3.6 mmol) of tBoc-L-Ser(Bzl) was dissolved in 15 ml of methylene chloride. "Bzl" as used herein means a benzyl group. After adding 0.74 g of DCC, the mixture was stirred at room temperature for 30 minutes. Next, a methylene chloride solution containing 2.14 g (3 mmol) of compound (8) and 4.20 μl (3 mmol) of triethylamine was added and the mixture was stirred at room temperature for 8 hours. The dicyclohexyl urea thus precipitated was filtered and the filtrate was concentrated. The residue from the filrate was purified by silica gel chromatography (n-hexane/ethyl acetate =1/1) to give 2.0 g (2.28 mmol) of the compound (17) was obtained in a tBoc-protected form, having a yield of 76%.

1.9 g of this protected product was dissolved in 20 ml of methylene chloride. After adding 10 ml of trifluoroacetic acid, the mixture was stirred at room temperature for 30 minutes to remove the tBoc protecting group. After the completion of the stirring, the solvent was distilled off under reduced pressure. 20 ml of methanol and 150 mg of 10% palladium carbon were added to the residue and the mixture was hydrogenated at 30° C. under atmospheric pressure for 8 hours. After filtering off the catalyst, the filtrate was concentrated under reduced pressure. Then the residue was recrystallized from acetonitrile to thereby give 1.62 g (2.02 mmol) of the compound (17) having a yield of 93% and a liquid crystal phase transition point of 96° C.

SYNTHETIC EXAMPLE 6: SYNTHESIS OF COMPOUND (23)

680 mg of DCC was added to a solution of methylene chloride (15 ml) and DMF (15 ml) containing 766 mg (3.3 mmol) of tBoc-L-Asn, 2.14 g (3 mmol) of the compound (8), 505 mg (3.3 mmol) of N-hydroxybenztriazole monohydrate and 420 μl (3 mmol) of triethylamine. The mixture was then stirred at room temperature for 7 hours.

After filtering the dicyclohexyl urea thus precipitated, the methylene chloride was distilled off from the filtrate under reduced pressure. Then 30 ml of ethyl acetate was added to the residue followed by successively washing with a 4% aqueous solution of sodium hydrogencarbonate, water and saline to separate. The ethyl acetate was distilled off under reduced pressure and the residue was purified by silica gel column chromatography (chloroform/methanol =10/1). Thus 2.08 g (2.56 mmol) of the compound (23) was obtained in a tBoc-protected form having a yield of 85%.

1.3 g (1.6 mmol) of this protected product as compound (23) was then dissolved in 15 ml of methylene chloride. After adding 7 ml of trifluoroacetic acid, the mixture was stirred at room temperature for 30 minutes. Then the solvent was distilled off under reduced pressure and the residue was recrystallized from acetonitrile. Thus 1.22 g (1.48 mmol) of the compound (23) was obtained having a yield of 92% and a liquid crystal phase transition point of 69° C.

SYNTHETIC EXAMPLE 7: SYNTHESIS OF COMPOUND (21)

The same condensation reaction as the one described in Synthetic Example 5 was performed except that 1.06 g (3.6 mmol) of the tBoc-L-Ser(Bzl) was replaced with 1.3 g (3.6 mmol) of Z-L-Asp(OBzl). After purifying by silica gel column chromatography (n-hexane/ethyl acetate =1/1), 1.6 g (1.7 mmol) of the compound (21) was obtained in a protected form having a yield of 57%.

1.5 g (1.6 mmol) of this protected product as compound (21) was dissolved in a solvent mixture comprising 10 ml of ethyl acetate and 20 ml of methanol. After adding 160 mg of 10 % palladium carbon, the mixture was hydrogenated at 30° C. under atmospheric pressure for 4 hours. After completion of the hydrogenation, 20 ml of methanol and 50 mol of DMF were added and the mixture was heated to 80° C. The crystals thus precipitated were dissolved and the catalyst was filtered off. The filtrate was cooled with ice and the precipitate was collected by filtering. After washing with ethyl acetate, 400 mg (0.56 mmol) of the compound (21) was obtained having a yield of 35% and a liquid crystal phase transition point of 117° C.

SYNTHETIC EXAMPLE 8: SYNTHESIS OF COMPOUND (28)

The same condensation reaction as the one described in Synthetic Example 6 was performed, except that the tBoc-L-Asn was replaced with 770 mg (3.4 mmol) of the tBoc-GlyGly synthesized in Synthetic Example 1. After purifying by silica gel column chromatography (chloroform/methanol = 20/1), 2.0 g (2.46 mmol) of the compound (28) was obtained in a tBoc-protected form having a yield of 82%.

1.9 g (2.34 mmol) of this protected product as compound (28) was dissolved in 20 ml of methylene chloride. After adding 10 ml of trifluoroacetic acid, the mixture was stirred at room temperature for 30 minutes. Then the solvent was distilled off under reduced pressure and the residue was recrystallized from ethyl acetate. Thus 1.64 g (1.98 mmol) of the compound (28) was obtained having a yield of 85% and a liquid crystal phase transition point of 137° C.

SYNTHETIC EXAMPLE 9: SYNTHESIS OF COMPOUND (22)

4.3 g (5.58 mmol) of the compound (16) synthesized in Synthetic Example 2 was dispersed in 50 ml of ion-exchanged water. After adding 15 ml of 1 N aqueous solution of sodium hydroxide, the mixture was extracted with 300 ml of ethyl acetate and separated. The ethyl acetate phase was washed with water and saline, dried ovr magnesium sulfate and then concentrated under reduced pressure to thereby give a volume of approximately 30 ml. After cooling with ice, the crystals thus precipitated were collected by filtering. Thus 1.4 g (2.13 mmol) of the compound (22) was obtained in the form of a free amine.

400 mg (0.61 mmol) of this free amine product was dissolved in a solvent mixture comprising 20 ml of ethyl acetate and 6 ml of chloroform and stirred. When 100 μl of conc. hydrochloric acid was added, a white precipitate was rapidly formed. Then 6 ml of methanol was added and the mixture was heated to approximately 70° C. to give a homogeneous solution. After allowing to cooling to room temperature, 380 mg (0.549 mmol) of the compound (22) thus precipitated was collected by filtering having a yield of 90% and a liquid crystal phase transition point of 135° C.

SYNTHETIC EXAMPLE 10: SYNTHESIS OF COMPOUND (14)

The same condensation and deprotection procedures as those described in Synthetic Example 1 were performed except that the 1,2-o-ditetradecyl-syn-glycerol was replaced with 1,2-o-dipalmitoyl-syn-glycerol. Thus the compound (14) was obtained having a liquid crystal phase transition point of 85° C.

SYNTHETIC EXAMPLE 11: SYNTHESIS OF COMPOUND (6)

Commercially available GlyGly was converted into Z-GlyGly in accordance with a known method, described, e.g., in "Peptide Gosei no Kiso to Jikken," ed. by Izumiya et al., (Maruzen).

The same condensation procedure as the one described in Synthetic Example 1 was performed, except that the tBoc-GlyGly was replaced with Z-GlyGly. Thus the compound (6) was obtained in a Z-protected form.

2.93 g (4 mmol) of this protected product as compound (6) was dissolved in a solvent mixture comprising 20 ml of methanol, 20 ml of ethyl acetate and 430 μl of concentrated hydrochloric acid. After adding 400 mg of 5% palladium carbon, the mixture was hydrogenated at room temperature under atmospheric pressure for 2 hours. As the reaction proceeded, a white precipitate was formed. After the completion of the reaction, the crystals thus precipitated were dissolved by heating and then the catalyst was filtered off. The solvent was distilled off from the filtrate under reduced pressure and the residue was recrystallized from ethyl acetate. Thus 2.23 g (3.4 mmol) of the compound (6) was obtained having a yield of 58% and a liquid crystal phase transition point of 91° C.

SYNTHETIC EXAMPLE 12: SYNTHESIS OF COMPOUND (12)

The same condensation and deprotection procedures as those described in Synthetic Example 11 were performed except that the 1,2-o-ditetradecyl-syn-glycerol was replaced with 1,2-o-dimyristoyl-syn-glycerol. Thus the compound (12) was obtained having a liquid crystal phase transition point of 95° C.

SYNTHETIC EXAMPLE 13: SYNTHESIS OF COMPOUND (14)

The same condensation and deprotection procedures as those described in Synthetic Example 11 were performed except that the 1,2-o-ditetradecyl-syn-glycerol was replaced with 1,2-o-dipalmitoyl-syn-glycerol. Thus the compound (14) was obtained having a liquid crystal phase transition point of 100° C.

SYNTHETIC EXAMPLE 14: SYNTHESIS OF COMPOUND (31)

710 mg (2.4 mmol) of tBoc-Ser(Bzl), 1 g (2.06 mmol) of 1,2-o-ditetradecyl-syn-glycerol and 24 mg of N,N-dimethylaminopyridine were dissolved in 15 ml of methylene chloride. To the obtained solution was added 460 mg of DCC under ice and stirring. Then the mixture was stirred under ice for 2 hours and at room temperature overnight. The dicyclohexyl urea thus precipitated was filtered and the solvent was distilled off from the filtrate under reduced pressure. To the residue, were added ethyl acetate and a 4% aqueous solution of sodium carbonate followed by extracting and separating. The organic phase was successively washed with a 10% aqueous solution of citric acid, water and saline and dried over sodium sulfate. After distilling off the ethyl acetate under reduced pressure, product.

To the residue, were added 10 ml of methylene chloride and 5 ml of trifluoroacetic acid and the mixture was stirred at room temperature for 30 minutes. After distilling off the solvent under reduced pressure, ethyl acetate and a 4% aqueous solution of sodium carbonate were added to the residue followed by extracting and separating. The organic phase was successively washed with water and saline and dried over sodium sulfate. After distilling off the ethyl acetate under reduced pressure, product.

To the residue, were added 710 mg of Z-Ser(tBoc), 310 mg of 1-hydroxynbenztriazole monohydrate, 10 ml of methylene chloride and 5 ml of DMF. The obtained solution was stirred under ice After adding 460 ml of DCC, the mixture was stirred under ice for 2 hours and at room temperature overnight. After treating in the same manner, the residue was purified by silica gel column chromatography (n-hexane/ethyl acetate=3/1). Thus 1.63 g (1.66 mmol) of was obtained having a yield of 80.5% (3 steps).

1.53 g (1.56 mmol) of this protected product was treated with trifluoroacetic acid in the same manner as the one described in Synthetic Example 1 to thereby remove the tBoc protecting group. Then the product was hydrogenated in the presence of hydrochloric acid in the same manner as the one described in Synthetic Example 11 to remove the benzyl-protecting group. Finally, the obtained compound (31) was recrystallized from a solvent mixture comprising ethyl acetate and methanol (10/1). Thus 770 mg (1.11 mmol) of the compound (31) was obtained having a yield of 71% (2 steps) and a liquid crystal phase transition point of 85° C.

SYNTHETIC EXAMPLE 15: SYNTHESIS OF COMPOUND (5)

The compound (5) was synthesized through the following pathway.

(5c)

SYNTHESIS OF COMPOUND (5a)

30 ml of a pyridine solution containing 7.3 g (15 mmol) of 1,2-o-ditetradecyl-syn-glycerol and 190 mg of N,N-dimethylaminopyridine was stirred under ice-cooling and 3 g (15.6 mmol) of p-toluenesulfonyl chloride was added thereto. After stirring at room temperature overnight, the reaction mixture was added to 40 ml of conc. hydrochloric acid diluted with 200 ml of water. The white precipitate thus formed was extracted and separated. Next, the organic phase was successively washed with water and saline and dried over sodium sulfate. After distilling off the ethyl acetate under reduced pressure, the residue was recrystallized from acetonirile. Thus 8.1 g (12.7 mmol) of the compound (5a) was obtained having a yield of 85%.

SYNTHESIS OF COMPOUND (5b)

5.12 g (8 mmol) of the compound (5a) and 2.78 g (15 mmol) of phthalimide potassium were dissolved in 30 ml of DMF and stirred at 120° C. for 1 hour. After cooling to room temperature, 100 ml of ethyl acetate was added thereto and the insoluble matters were filtered off. The filtrate was successively washed with a 4% aqueous solution of sodium carbonate, water and saline and then dried over sodium sulfate. After distilling off the ethyl acetate under reduced pressure, the residue was purified by silica gel column chromatography (n-hexane/ethyl acetate =15/1). Thus 4.5 g (7.3 mmol) of the compound (5b) was obtained having a yield of 91%.

SYNTHESIS OF COMPOUND (5c)

Figure 1:
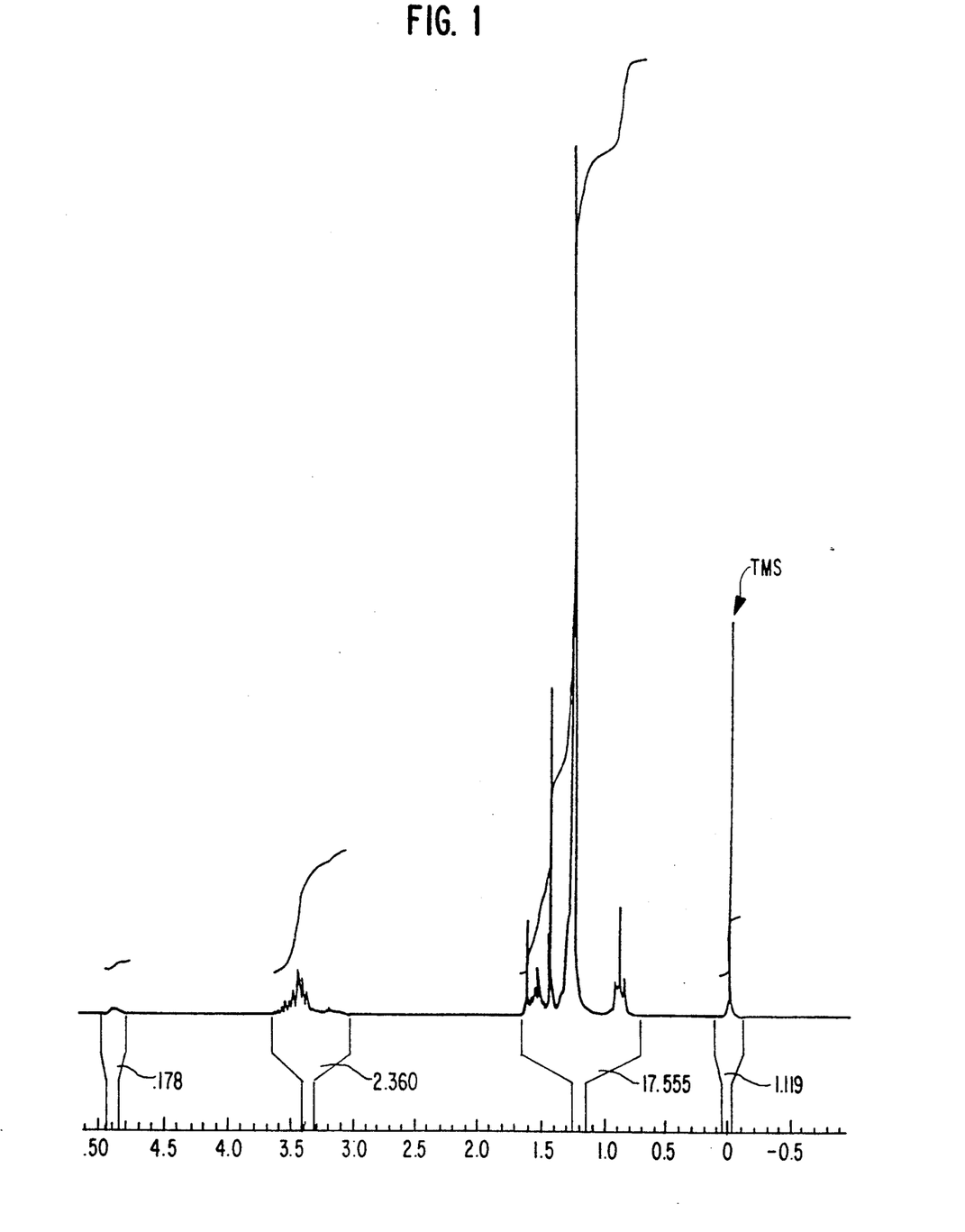
FIG. 1 is a graph showing the $^1H$ NMR spectrum of the intermediate 5C [a compound involved in the general formula (II)] of the compound (5) described in Synthetic Example 15.

30 ml of an ethanol solution containing 4.3 g (7 mmol) of the compound (5b) and 0.7 g (14 mmol) of hydrazine monohydrate was stirred under reflux for 2 hours. After cooling by allowing to stand, 1.7 ml of conc. hydrochloric acid was added thereto. Then the ethanol was distilled off under reduced pressure and 50 ml of ethyl acetate and 50 ml of water were added to the residue followed by extracting and separating. The ethyl acetate phase was washed with a 1 N aqueous solution of sodium hydroxide and 2.2 g (10 mmol) of di-t-butyl dicarbonate was added thereto. After stirring at room temperature for 2 hours, the ethyl acetate solution was successively washed with a 4% aqueous solution of sodium hydrogencarbonate and saline. After concentrating the ethyl acetate under reduced pressure, the residue was purified by silica gel column chromatography (n-hexane/ethyl acetate=5/1). Thus 2.42 g (4.1 mmol) of the compound (5c) was obtained as an amorphous product having a yield of 59%. FIG. 1 shows the $^1$H NMR spectrum (20 mHz) of this compound in heavy chloroform.

SYNTHESIS OF COMPOUND (5)

1.88 g (3.2 mmol) of the compound (5c) was dissolved in 20 ml of methylene chloride. After adding 10 ml of trifluoroacetic acid, the mixture was stirred at room temperature for 1 hour.

After distilling off the solvent under reduced pressure, ethyl acetate was added to the residue followed by successively washing with a 1 N aqueous solution of sodium hydroxide and saline. Then it was dried over magnesium sulfate and the ethyl acetate was distilled off under reduced pressure. Thus 1.47 g (3.04 mmol) of the compound (5d) was obtained as a waxy product having a yield of 95%. This compound showed 484 (M+ +H) in FAB-MS. The compound (5d) was employed in the following reaction without purifying.

1.37 g (2.83 mmol) of the compound (5d), 0.74 g (3.2 mmol) of tBoc-GlyGly and 0.49 g (3.2 mmol) of hydroxylbenztriazole monohydrate were dissolved in a solvent mixture of 15 ml of methylene chloride and 15 ml of DMF. Then 0.66 g of DCC was added thereto under cooling with water and the mixture was stirred overnight. The dicyclohexyl urea thus formed was filtered and the methylene chloride was distilled off under reduced pressure. Ethyl acetate was added to the residue followed by successively washing with a 4% aqueous solution of sodium carbonate and a 10% aqueous solution of citric acid. After distilling off the ethyl acetate under reduced pressure, the residue was purified by silica gel column chromatography (ethyl acetate/n-hexane =8/1). Thus 1.74 g (2.49 mmol) of the compound (5) was obtained in a tBoc-protected form having a yield of 82%.

1.66 g of this protected product was dissolved in 16 ml of methylene chloride. After adding 8 ml of trifluoroacetic acid, the mixture was stirred at room temperature for 30 minutes. Then the solvent was distilled off under reduced pressure and the residue was recrystallized from ethyl acetate. Thus 1.1 g (1.54 mmol) of the compound (5) was obtained having a yield of 65% and a liquid crystal phase transition point of 96° C.

Liposomes comprising the compound (I) of the present invention may be prepared by known methods.

That is to say, the liposome of the present invention may be prepared by any known methods without restriction, for example, a vortexing method [A.D. Bangham, J. Mol. Biol., 13, 238 (1965),] a sonication method [C. Huang. Biochem., 8, 344 (1969),] a prevesicle method [H. Trauble, Neurosci. Res. Prog. Bull., 9, 273 (1971),] an ethanol-injection method [S. Batzri, Biochem. Biophys. Acta., 298, 1015 (1973),] a French press extraction method [Y. Barenhollz, FEBS. Lett., 99, 210 (1979),] a cholic acid removal method [Y. Kagawa, J. Biol. Chem., 246, 5477 (1971),] a Triton X-100 batch method [W. J. Gerritsen, Eur. J. Biochem., 85, 255 (1978),] a Ca$^{2+}$fusion method [D. PaPahadjopoulos, Biochem. Biophys. Acta., 394, 483 (1975),] an ether injection method [D. Deamer, Biochem. Biophys. Acta., 443, 629 (1976),] an annealing method [R. Lawaczeck, Biochem. Biophys. Acta., 443, 313 (1976),] a freeze-melt fusion method [M. Kasahara, J. Biol. Chem., 252, 7384 (1977).] a W/O/W emulsion method [S. Matsumoto, J. Colloid Interface Sci., 62, 149 (1977),] a reverse-phase evaporation method (F. Szoka, Proc. Natl. Acad. Sci. USA, 75, 4194 (1978),] a high-pressure emulsifying method [E. Mayhew, Biochem. Biophys. Acta., 775, 169 (1984)] as well as those described in JP-A-60-7932, JP-A-60-7933, JP-A-60-7934, JP-A-60-12127 and JP-A-62-152531.

The substance to be encapsulated in the present invention may be either a hydrophilic drug or a lipophilic one. Furthermore, both of these drugs may be encapsulated simultaneously. Examples of hydrophilic drugs include anticancer agents such as adriamycin, actinomycin, mitomycin, 1$\beta$-arabinofurasylcytosine, bleomycin and cisplatin, antiviral agents such as interferon, aminoglycosides such as gentamycin, antibiotics such as $\beta$-lactam compounds (for example, sulbenicillin, cefoiam, and cefmenoxine), peptide hormones such as TRH and insulin, enzymes such as lysozyme, asparaginase and glycoxidase, immunopotentiators such as muramyl dipeptide and muramyl tripeptide and proteins such as immunoglobulin and various toxins.

Examples of the lipophilic drug include anticancer agents such as ansamytocin, immunopotentiators such as TMD-66 [Gann 74 (2), 192–195 (1983)] and MTP-PE (JP-A-59-163389) and phospholipid derivatives (JP-A-59-163389).

In addition, substances other than drugs (for example, marker, plasmid, DNA, RNA) may be used in the present invention without restriction, so long as they are useful when administered to living organisms.

As the solution to be encapsulated, an aqueous solution prepared by dissolving an appropriate water-soluble substance in water may be used. In some cases, a solution prepared by simply dissolving a drug in water may be used. Examples of the water-soluble substances include known buffers (for example, phosphate buffer, citrate buffer), various salts (for example, sodium chloride, monosodium phosphate, disodium phosphate), saccharides (for example, glucose) and amino acids (for example, l-arginine). Either one of these substances or a mixture thereof may be used.

The solution to be encapsulated may further contain a preservative (for example, paraben), if required.

The unencapsulated drug may easily be separated from liposomes by, for example, by known methods such as dialysis, filtration such as ultrafiltration or centrifugation. In this case, it is preferable to approximate the osmotic pressure of the internal aqueous phase to that of the external one as close as possible.

Either one of the compounds of the present invention or a mixture thereof may be used. Further, other liposome film-forming lipids may be used together. Various phospholipids, sphingolipids or synthetic lipids may be used therefore.

In order to further strengthen the film structure, various methods known in the art of phospholipid liposomes may be employed together.

Typical examples of these methods include those comprising mixing sterol or cholesterol or coating with a polysaccharide polymer (JP-A-61-69801).

Compounds of the present invention can form stable liposomes, though the radius of hydration of the hydrophilic moiety thereof is not so large as those of conventional bilayer film-forming lipids. This could be achieved by the intermolecular hydrogen bonds in the peptide region.

When the compound of the present invention of the general formula (I) forms a monolayer at a gas/liquid interface, the oligopeptide region of the compound forms a completely stretched conformation and thus forms a hydrogen bond together with the adjacent peptide bond so as to cause a two-dimensional orientation.

This interaction contributes to the formation of a highly dense film having a small molecular volume, compared with a phospholipid having the same hydrophobic chain.

Films of the present invention, which have a domain formed by the oriented oligopeptide, can efficiently incorporate proteins such as enzymes, antigens, antibodies and receptors.

Examples of such enzymes include oxidation-reduction enzymes such as glucose oxidase, amino acid oxidase, catalase, ascorbate oxidase, xanthine oxidase, cholesterol oxidase, glycerol oxidase, glcyerol-3-phosphate oxidase, choline oxidase, acetyl CoA oxidase, aldehyde oxidase, galactose oxidase, sarcosine oxidase, pyruvate oxidase, lactate oxidase, tyrosinase, and peroxidase;

dehydrogenases such as alcohol dehydrogenase, glycerol dehydrogenase, glutamate dehydrogenase, lactate dehydrogenase, malate dehydrogenase, formaldehyde dehydrogenase, 3-a-hydroxysteroid dehydrogenase and cholesterol dehydrogenase;

transferases such as creatine kinase, pyruvate kinase, hexokinase, glycerol kinase, myokinase and fructokinase;

hydrolases such as urease, uricase, asparaginase, amylase, lipase, phospholipase, phosphatase, lactase, arginase, urokinase, esterase, trypsin, chymotrypsin, pectinase and penicillinase;

isomerases such as citrate lyase, decarboxylase, fumarase, aspartase and glucose phosphate isomerase; and lygases such as glutathione synthetase and pyruvate synthetase.

Examples of antigens and antibodies that can be used with films of the present invention include, a number of substances including serum albumin, syphilitic antibody, chorionic gonadotropin, and a α-fetoprotein. These substances are classified and described in "Meneki no Kenkyu" [ed. by Y. Yamamura, Kobun Shoin (1986),] the contents of which are incorporated by reference.

In addition, biofunctional substances such as hemeproteins (for example, hemoglobin, cytochrome C) and metal complexes including porphyrin derivatives such as chlorphyrin can also be used with films of the present invention. Furthermore, water-soluble proteins such as albumin can be used.

Examples of solvents for developing monolayer films to be used in the present invention include common volatile nonpolar organic solvents such as chloroform, dichloromethane, benzene, toluene and ether as well as mixtures thereof, together with polar hydrophilic solvents such as alcohols and water.

Examples of subphases for preparing monolayers of the present invention include buffer solutions of various pH values and solutions of various metal salts such as calcium, barium, cadmium, potassium and sodium salts. The temperature of the subphase may be appropriately controlled according to known procedures, if required. The subphase may be fluidized by, for example, stirring or vibrated to thereby facilitate the reaction between the molecule for forming the monolayer and the compounds contained in the subphase. In the preparation of the monolayer film, the atmosphere on the subphase may be replaced with an inert gas such as $N_2$ or Ar to thereby prevent the monolayer from oxidation or deterioration.

The monolayer thus formed on the water surface may be built up onto the surface of a base or a substrate by various known laminating methods including the aforesaid L-B technique. The L-B technique, which is a vertical build-up method, is described in, for example, J. A. Chem. Soc., 57, 1007 (1935); G. L. Gains Jr., "Insoluble Monolayers at Liquid-Gas Interfaces," Interscience, New York (1966); and K. Fukuda, "Zairyo Gijutsu", 4, 261 (1986).

In addition to the L-B technique, various build-up methods including vertical build-up method and rotational build-up method (refer to, for example, JP-A-60-189929, JP-A-61-42394) may be employed. Multilayers may be obtained by repeatedly building up a monolayer on a substrate. A continuous lamination method described in, for example, JP-A-60-209245 may be used therefore. In this case, it is preferable that at least some portion of the host compound of the present invention is contained in the most external molecular layer. Molecular layers located close to the substrate, compared with the aforesaid layer, may consist of other organic amphipatic compounds (surfactant-type molecules).

The substrate (base) to be used in the formation of a monolayer or multilayers by the L-B technique in the present invention may be selected from among electrical conductors such as various metals, inorganic insulating materials such as vitreous inorganic materials (for example, glass, quartz), various organic and inorganic crystals, inorganic semiconductors (for example, $SnO_2$, $In_2O_3$, $ZnO$, $TiO_2$, $WO_3$, $GaAs$, $Si$), organic semiconductors, organic conductors, organic polymers and composite materials consisting the above-mentioned ones. This material may be an electrode connected to an external electrical circuit or other sensors (for example, field effect mode transducer). The surface of the material may be physically or chemically treated by various methods so as to make hydrophilic or hydrophobic. An example of a hydrophobic treatment comprises reacting the surface of the substrate with an alkylsilane derivative which is employed as a coupling agent.

In the structure of film materials of the present invention, the surface of the substrate or base may be chemically bound to molecules constituting the multilayers in contact therewith. Such bonds may be formed through a thermal chemical reaction between a reactive group (for example, hydroxyl group) on the surface of the substrate and the terminal reactive group (for example, active silane) of the molecule constituting the multilayers.

The compound of the general formula (I) to be used in the present invention may be mixed with a film-forming compound, which is a reactive compound useful in binding a functional guest compound, for example, those described in JP-A-63-171642, JP-A-1-4246 and JP-A-1-56783.

The present invention, wherein an arbitrary functional compound (for example, enzyme, protein) may be fixed on the surface of an ultra-thin film and then a highly efficient chemical reaction (for example, catalytic reaction, photochemical response, oxidation/reduction) or a physical change (for example, optical change, electrical change) shown by the functional compound can be monitored, and is available and known in various fields including the formation of sensor image, information recording and energy conversion, and thus is highly useful.

To further illustrate the present invention, and not by way of limitation, the following Examples of liposomes and films according to the present invention will be given.

EXAMPLE 1

30 mg of the compound (22) was dissolved in 10 ml of chloroform. After distilling off the chloroform with a rotary evaporator, the residue was further dried in vacuo to thereby form a film of the compound (22). 3 ml of a tris buffer solution (6 mM, pH 7.0) containing 150 mM of sodium chloride was added thereto followed by performing Vortex dispersion. After performing ultrasonic irradiation of bath-type at 50° C. for 10 minutes, the dispersion was heated to 80° C. for 10 minutes. Then it was filtered 6 times with the use of an extruder (0.2 μ polycarbonate filter, 55° C.) under elevated pressure (about 11 kg/cm$^2$). When the particle size was measured with a NICOMP, a single dispersion mode particle size distribution (average 149 nm) was obtained. Then the dispersion was stained with phosphotungstic acid and observed with a TEM. Thus it was confirmed that the vesicle consisted of a singly layer.

EXAMPLE 2

A vortex dispersion obtained by the same method as the one described in Example 1 was subjected to ultrasonic irradiation of probe type (30 W, 5 minutes). Then it was confirmed, in the same manner as the one described in Example 1, that a monolayer vesicle of an average particle size of approximately 80 nm was formed.

EXAMPLE 3

The gel/liquid crystal transition point of a compound of the present invention in pure water was measured with a Privalov type DSC. Table 1 shows the results.

TABLE 1

| Compound | Transition point (°C.) |
|---|---|
| 5 | 50 |
| 6 | 59 (59) |
| 16 | 53 (57) |
| 20 | 48 |
| 21 | 61 |
| 22 | 57 |
| 23 | 49 |
| 28 | 47 |

Figures given in parentheses show data determined in a tris buffer solution (6 mM, pH 7.0).

EXAMPLE 4

By using 30 mg of the compound (6), a film was formed in the same manner as the one described in Example 1. Next, 3 ml of a tris buffer solution (6 mM, pH 7.0) containing 50 mM of safranine-O and 200 mM of glucose was added thereto. Then it was subjected to Vortex-dispersing and ultrasonic treatment (bath-type), heated to 80° C. and then treated with an extruder, similar to the procedure of Example 1. The dispersion was subjected to gel-filtration by using Sephadex G-50 equilibrated with a tris buffer solution containing 150 mM of sodium chloride. Thus the unencapsulted safranine-O was separated.

The lipid fraction (average particle size 140 nm) thus obtained was incubated at 37° C. and the leaking safranine-O was determined by fluorometry. For comparison, the above procedure was repeated except that the compound 6 was replaced with dipalmitoylphosphatidylcholine (DPPC) to thereby give liposomes (average particle size 60 nm) containing safranine-O. These liposomes were also incubated at 37° C. and the leaking safranine-O was determined.

Figure 2:
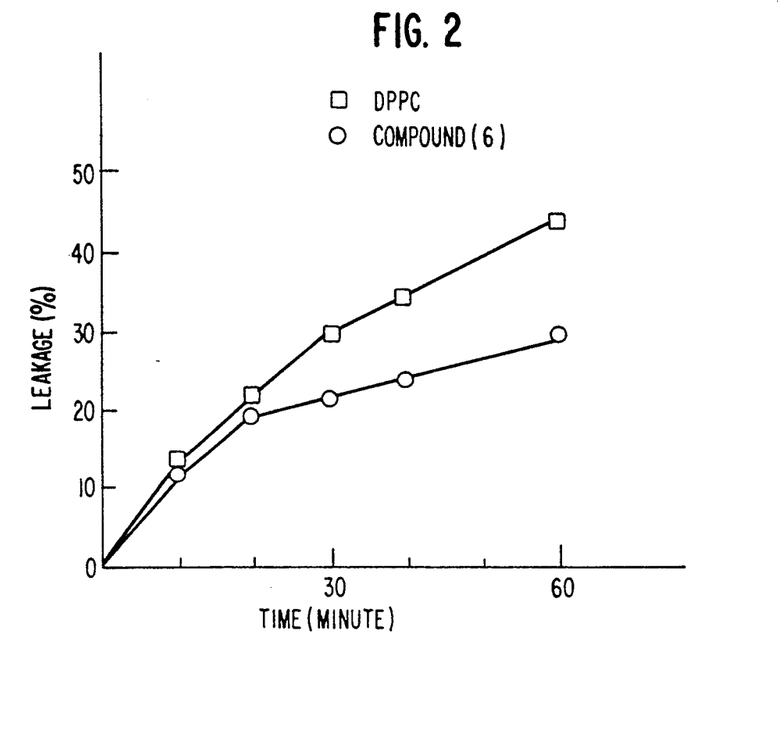
FIGS. 2 and 3 are graphs each showing the extent of leakage of a content included in a liposome.

FIG. 2 shows the results.

As FIG. 2 shows, the liposomes comprising the compound (6) of the present invention as a film component is superior to the ones comprising DPPC, which is a natural phospholipid, in barrier function on safranine-O.

EXAMPLE 5

Liposomes containing safranine-O were prepared in the same manner as the one described in Example 4, except that the compound (6) was replaced with the compounds (8), (11), (14) and (22). Then the leakage of the safranine-O at 37° C. was examined. Table 2 shows the leakage ratios of the safranine-O after 1 hour.

TABLE 2

| Lipid | Leakage ratio (%) |
|---|---|
| 6 | 30 |
| 8 | 41 |
| 11 | 51 |
| 14 | 37 |
| 22 | 46 |
| DPPC | 44 |

As Table 2 shows, the compounds of the present invention are comparable or superior to DPPC, which is a natural phospholipid, in barrier function.

EXAMPLE 6

The procedure of Example 4 was repeated except that the compound (6) was replaced with the compound (16) to thereby give liposomes containing safranine-O. These liposomes were incubated at 4° C. Liposomes containing safranine-O prepared by using DPPC showed the formation of a precipitation when stored at 4° C. for 20 days. On the other hand, those prepared by using the compound (16) maintained a stable dispersion state after 4 months. After 80 days, these liposomes showed a leakage ratio of the safranine-O of as low as 6%.

EXAMPLE 7

Figure 3:
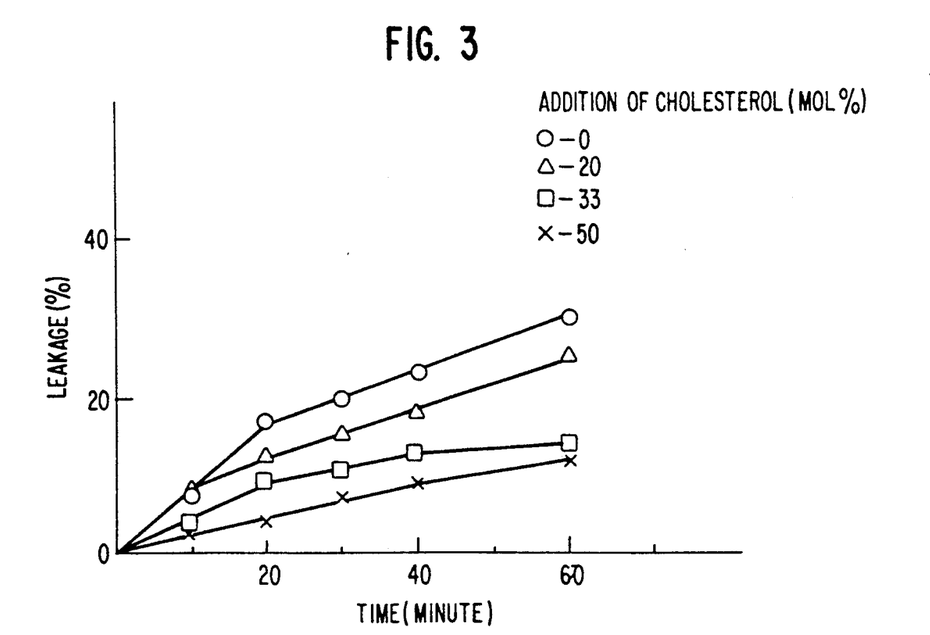

The procedure of Example 4 was repeated except that 20, 33 and 50% by mol of cholesterol was added to the compound (6). Thus liposomes containing safranine-O were prepared. These liposomes were incubated at 37° C. and the leaking safranine-O was determined by fluorometry. FIG. 3 shows the results.

As FIG. 3 shows, the barrier function of the liposome comprising the compound of the present invention can be remarkably elevated by adding cholesterol. Further, it was confirmed by using a Privalov type DSC that the gel/liquid crystal transition point of the compound (6) disappeared when 50% of cholesterol was added.

EXAMPLE 8

90 mg of the compound (16) was added to 9 ml of a tris buffer solution (6 mM, pH 7.0) containing 270 mM of glucose and then the mixture was dispersed for 1 minute thrice with the use of a homogenizer (8000 rpm). The obtained dispersion was heated to 50° C. for 10 minutes and then to 80° C. for 10 minutes, followed by performing ultrasonic irradiation of bath type at 55° C. for 10 minutes. After heating to 80° C. for 10 minutes again, the dispersion was filtered six times with the use of an extruder (0.1μpolycarbonate filter, 59° C.) under elevated pressure (approximately 15 kg/cm$^2$). The filtrate was gel-filtered through Sephadex G-50 (tris buffer solution, 6 mM, pH 7.0) to thereby separate the unencapsulated glucose. The average particle size of the lipid associate fraction thus obtained was 90 nm. Further, the fraction was negative-stained with phosphotungstic acid and then observed under an electron microscope. Thus it was confirmed that monolayer vesicles were formed.

This fraction was incubated at 37° C. for 60 minutes and then ultracenytrifuged at 20° C. at 25,000 rpm for 30 minutes. When the glucose concentration of the supernatant was examined by enzymatic colorimetry, it was found out that the leakage ratio of glucose was 2%. (Triton X was added to the gel-filtered fraction to thereby break the vesicles. Then the glucose concentration thus determined by colorimetry was referred to as 100%.)

EXAMPLE 9

The FTIR spectrum of the compound (22) was determined under the following conditions.

(1) KBr pellet.
(2) 10 mM chloroform solution.
(3) Vesicles prepared in heavy water.

Table 3 shows the absorption of the carbonyl stretch vibration of the amide.

TABLE 3

| Condition | $VC = O\ (cm^{-1})$ |
|---|---|
| (1) | 1643 |
| (2) | 1673 |
| (3) | 1657 |

Table 3 suggests the presence of a hydrogen bond between amido bonds which seemingly contributes to the formation of stable vesicles by the compound of the present invention.

Now, the production of a film comprising the compound (I) of the present invention will be described.

EXAMPLE 10

The compound (6) was dissolved in a solvent mixture of chloroform and methanol (4 : 1 v/v) to thereby give a $10^{-3}$ M solution. Then the obtained solution was developed on a $10^{-3}$ M tris buffer solution (pH 7.0) to thereby form a single dispersion film. The monolayer formed on the surface of water was slowly compressed with a belt-drive system barrier at 25° C. and thus the surface pressure/molecular occupation area ($\pi$-A) properties were determined. As a result, the curve shown in FIG. 4 was obtained.

Figure 5:
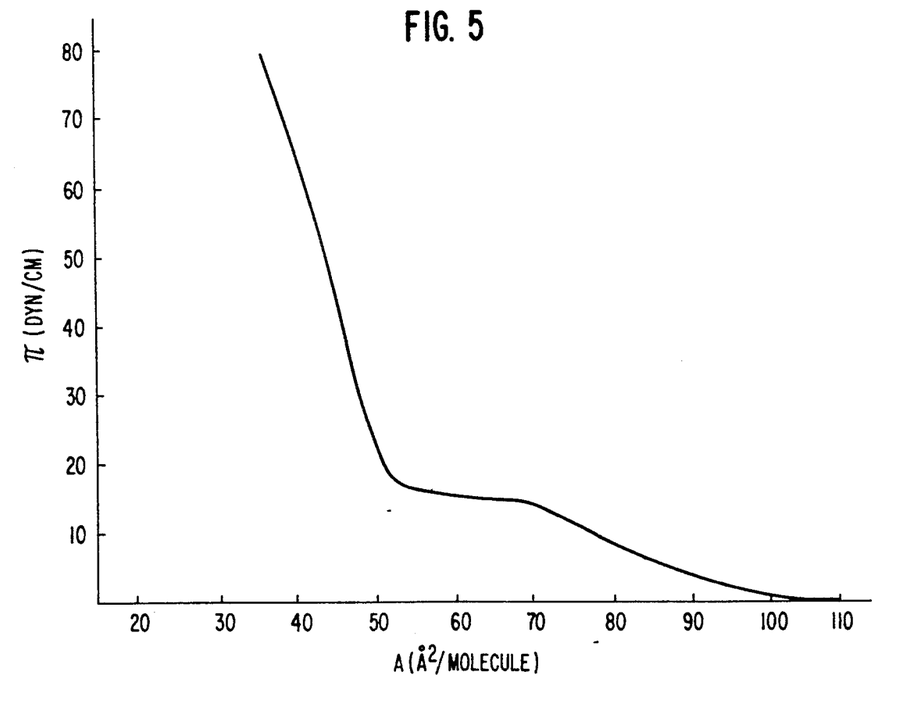
Figure 6:
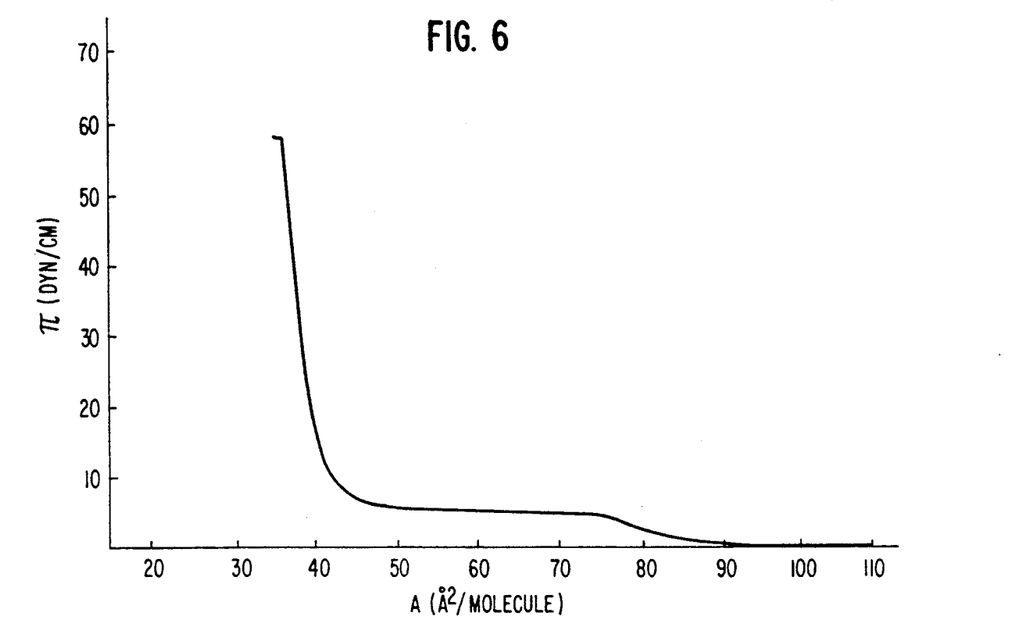
Figure 7:
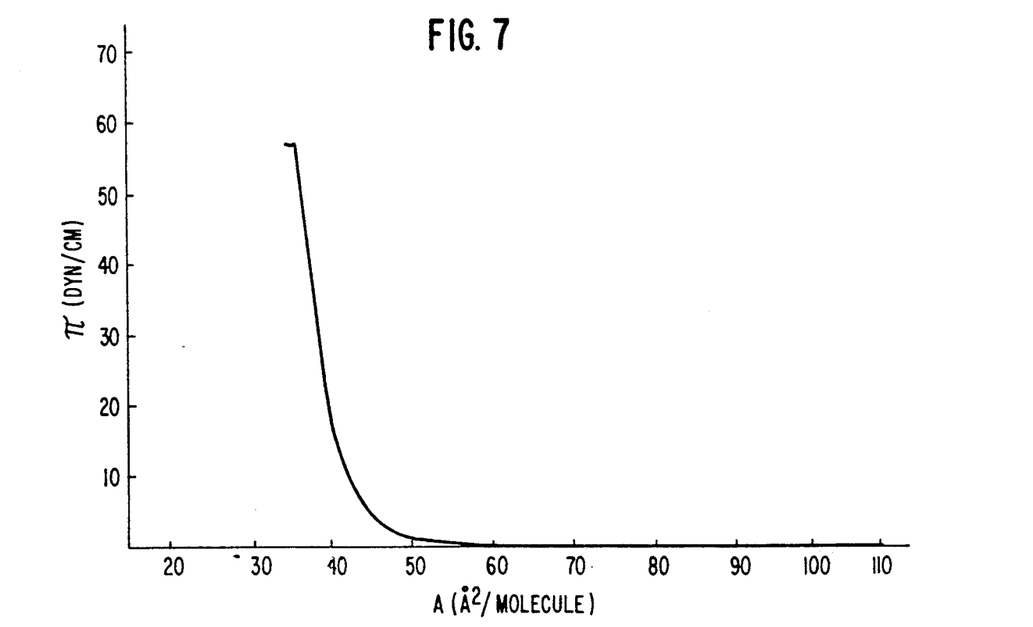
Figure 8:
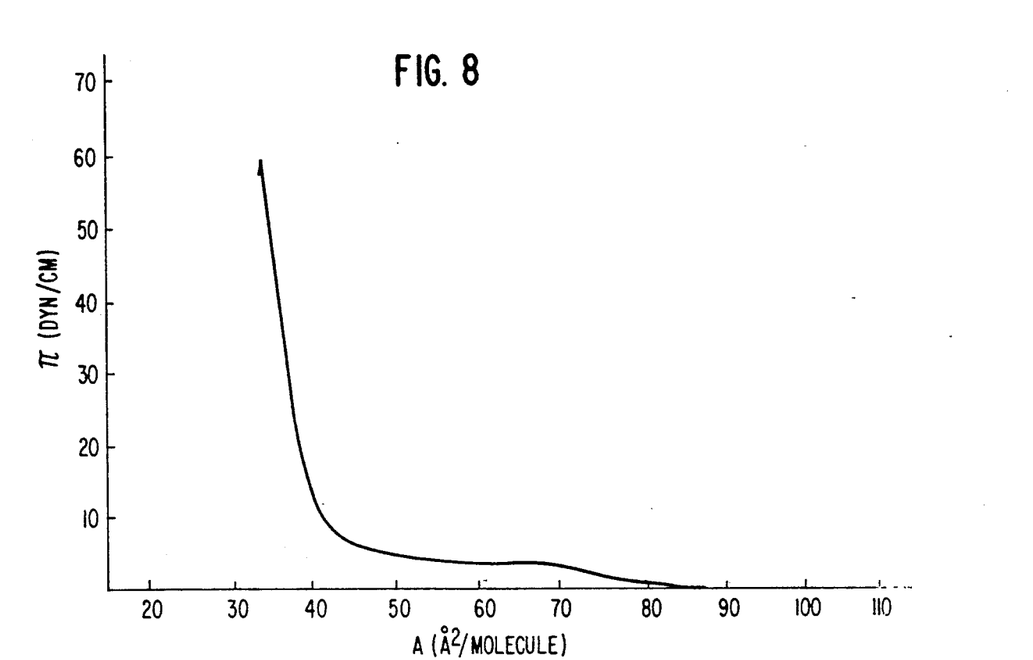
Figure 9:
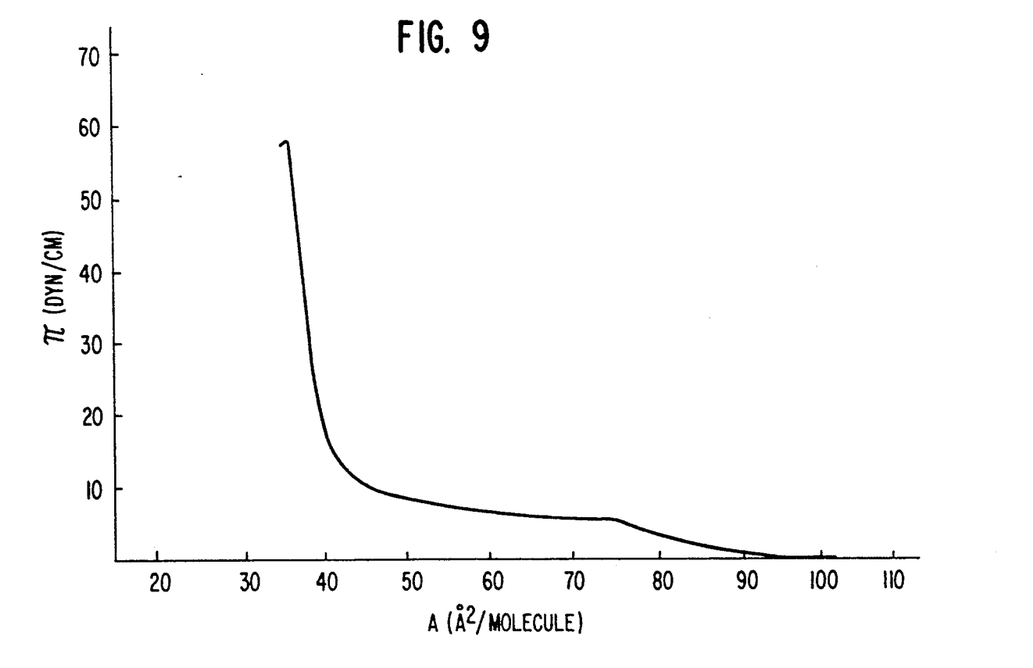

For comparison, the $\pi$-A properties of di-o-hexadecyl-syn-phosphatidylcholine (DHPC) were determined under the same conditions. FIG. 5 shows the result.

Figure 4:
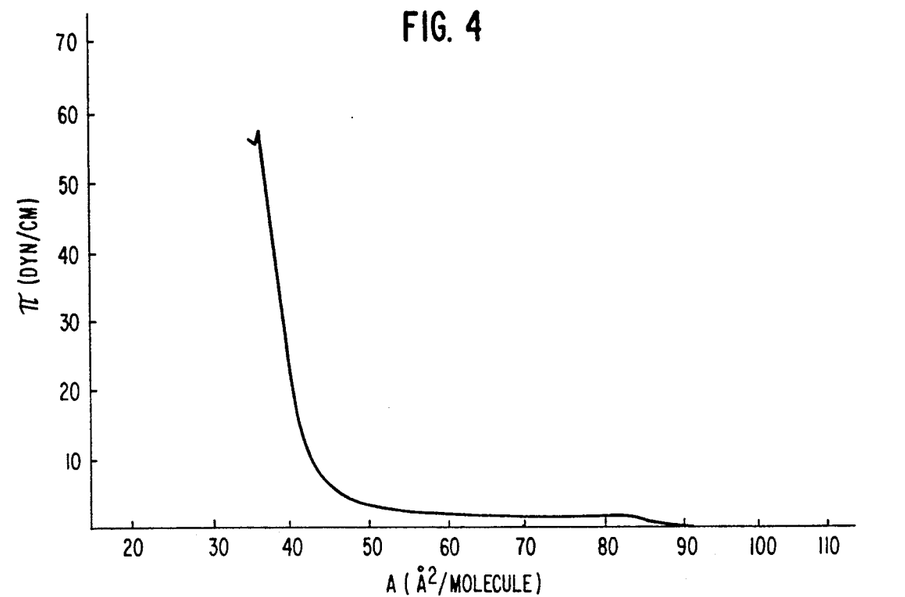
FIGS. 4 to 9 are graphs each showing the relationship between the surface pressure vs. molecular occupation area of a monolayer.

The comparison of these Figs. indicate that the compound of the present invention formed a highly dense and thick monolayer which gives a $\pi$-A curve having a smaller molecular occupation area compared with the natural phospholipid having a hydrophobic moiety of the same structure (compound (6): 42 Å, DHPC: 55 Å) and showing a sharp rise-fall.

EXAMPLE 11

FIGS. 6, 7, 8 and 9 show respectively the $\pi$-A curves of the compounds (22), (16), (12) and (31) each formed in the same manner as the one of Example 10. These Figs. indicate that each of these compounds has similar characteristics as those of the compound (6) of Example 10.

EXAMPLE 12

A 1 mM solution of the compound (22) was developed on pure water and compressed to 30 dyn/cm. After controlling the surface pressure constantly, the film was transported onto a silicone substrate 20 times by the vertical immersion method. After sufficiently drying spontaneously, FT-IR was measured from the vertical direction to the surface of the substrate. As a result, the carbonyl absorption of the amido was 1663 $cm^{-1}$.

The amido absorption of the compound (22) in a dilute chloroform solution in the absence of any hydrogen bond was 1673 $cm^{-1}$. Therefore a shift toward the low wave length by 10 $cm^{-1}$ was observed in the state of multilayers. This shift might be caused by an intermolecular hydrogen bond between the adjacent oligopeptide.

While the invention has been described in detailed with reference to specific embodiments, it will be apparent to one skilled in the art that various changes and modifications can be made to the invention without departing from its spirit and scope.

What is claimed is:

1. A peptide derivative amphiphatic compound or N-terminal salt thereof represented by formula (I):

wherein $R^1$ and $R^2$ each represents a straight-chain or branched alkyl group having 8 to 24 carbon atoms optionally having a substituent or an unsaturated group, wherein each of said $R^1O$ moiety and $R^2O$ moiety in formula (I) form an ether linkage in said compound; X represents —O— or —NH—; $R^{3n}$ and $R^{3(n+1)}$ each represents an α-amino acid side chain; n is an integer of from 0 to 5; said compound may be a racemic compound or an optically active compound when said compound has an asymmetric carbon atom; and said N-terminal salt of said compound optionally forms with an acid component.

* * * * *